United States Patent [19]

Legrand et al.

[11] Patent Number: 4,845,290

[45] Date of Patent: Jul. 4, 1989

[54] PROCESS FOR THE PREPARATION OF HYDROXYLAMINES AND PRODUCTS THEREBY OBTAINED

[75] Inventors: Franz Legrand, Quaregnon; Paul Deschrijver, Asse-Zellik, both of Belgium

[73] Assignee: Interox (Société Anonyme), Brussels, Belgium

[21] Appl. No.: 15,387

[22] Filed: Feb. 17, 1987

[30] Foreign Application Priority Data

Feb. 17, 1986 [FR] France ................................ 86 02217

[51] Int. Cl.$^4$ .............................................. C07C 83/00
[52] U.S. Cl. .................................... 564/300; 564/301
[58] Field of Search ............... 564/297, 298, 299, 300, 564/301

[56] References Cited

U.S. PATENT DOCUMENTS

| | | | |
|---|---|---|---|
| 2,169,976 | 8/1939 | Guenther et al. | 564/301 X |
| 2,795,611 | 6/1957 | List | 564/300 |
| 3,232,990 | 2/1966 | Deger et al. | 564/301 |
| 3,243,462 | 3/1966 | Smith | 564/300 X |
| 3,277,019 | 10/1966 | Young | 564/301 X |
| 3,467,711 | 9/1969 | Bader et al. | 260/583 |

FOREIGN PATENT DOCUMENTS 8112797 12/1982 France .

*Primary Examiner*—Robert V. Hines
*Attorney, Agent, or Firm*—Spencer & Frank

[57] ABSTRACT

Secondary amines are oxidised with hydrogen peroxide in the presence of a catalyst chosen from derivatives of zinc or cadmium.

The process is applied to the preparation of di-substituted N,N-hydroxylamines such as N,N-diethylhydroxylamines and N,N-di-n-propylhydroxylamine.

7 Claims, No Drawings

PROCESS FOR THE PREPARATION OF HYDROXYLAMINES AND PRODUCTS THEREBY OBTAINED

FIELD OF THE INVENTION

The present invention relates to a process for the preparation of di-substituted N,N-hydroxylamines according to which a secondary amine is oxidised with hydrogen peroxide in a solvent medium and in the presence of a catalyst.

The invention also relates to di-substituted N,N-hydroxylamines obtained by said process.

TECHNOLOGY REVIEW

A process for synthesising dimethylhydroxylamine by oxidising dimethylamine with hydrogen peroxide in the presence of oxides of Se, Mo, W, V, U and derivatives of these oxides as catalysts has been known for a long time. These catalysts are, however, effective only for the oxidation of dimethylhydroxylamine alone and the yields obtained remain, however, low (U.S. Pat. No. 3,243,462 to Smith et al, column 2, lines 23 to 36 and lines 65 to 67 and column 3, example 3).

U.S. Pat. No. 3,467,711 to Bader et al teaches that the use of oxidation catalysts such as tungstates or vanadates is not suitable and the exclusive use of sequestering agents for metals catalysing the decomposition of hydrogen peroxide is advocated (column 2, lines 43 to 68 and columns 4 and 5, claim 1). The yields obtained by applying this method do not exceed 55% di-substituted N,N-hydroxylamine.

SUMMARY OF THE INVENTION

The present invention aims to provide a process for the preparation of di-substituted N,N-hydroxylamines which does not have the disadvantages of the known processes. Its aim, in particular, is to permit higher di-substituted N,N-hydroxylamine yields. Other aims of the invention are a simplification of the separation of the hydroxylamines from the reaction medium and a reduction in the cost of reagents by no longer prescribing the use of sequestering agents for metal ions.

To this end, the invention relates to a process for the preparation of di-substituted N,N-hydroxylamines according to which secondary amine is oxidised with hydrogen peroxide in the presence of a catalyst; according to the invention, the catalyst is chosen from compounds of zinc and cadmium.

The catalyst employed in the process according to the invention can consist of a derivative of zinc or cadmium. Of these derivatives, the salts, oxides and hydroxides of zinc or cadmium are highly suitable. Salts and hydroxides of zinc and cadmium which are particularly suitable are the halides and carbonates, especially the chlorides and hydroxycarbonates of zinc or cadmium.

According to the invention, the catalyst employed can also consist of an organic derivative of zinc or cadmium. The salts of carboxylic acids of zinc and cadmium are particularly suitable.

The catalyst must be employed in concentrations of at least 0.02 mmole per mole of amine to be oxidised. In principle, there is no upper limit to the quantity of catalyst employed. For economic reasons, it is not advisable in practice to exceed the quantity of 20 mmoles of catalyst per mole of amine. Advantageous quantities are those between 0.2 and 2.5 mmoles per mole of amine.

The catalyst can be added to the reaction medium in the pure state, in solution in water or in a solvent or in dispersion in these same media.

The invention applies to the oxidation of various types of secondary amines. It applies in particular to the oxidation of aliphatic secondary amines, aromatic secondary amines and cyclic secondary amines. Aliphatic secondary amines are particularly suitable, especially those where the two aliphatic groups attached to the nitrogen are straight chain or branched alkyl groups. These alkyl groups can be the same or different. Examples of such amines which are particularly suitable are N,N-dimethylamine, N,N-diethylamine, N-methyl,N-ethylamine, N,N-di-n-propylamine, N-methyl,N-n-propylamine, N-ethyl-,N-n-propylamine, N,N-di-isopropylamine, N-n-propyl,N-isopropylamine, N-methyl-,N-isopropylamine and N-ethyl-,N-isopropylamine, the list being non-limiting.

Of the aromatic secondary amines which can be oxidised according to the process of the invention, those in which the aromatic group is composed of an unsubstituted benzene nucleus are advantageous, such as, for example, N-methyl-,N-phenylamine, N-ethyl-,N-phenylamine, N-n-propyl-, N-phenylamine, N-isopropyl-,N-phenylamine and N,N-diphenylamine.

Within the class of cyclic secondary amines which can be used in the process according to the invention, those in which the cyclic group is composed of an unsubstituted cyclohexane group are highly suitable, such as, for example, N-methyl,N-cyclohexylamine, N-ethyl-,N-cyclohexylamine, N-n-propyl,N-cyclohexylamine, N-isopropyl,N-cyclohexylamine and N,N-dicyclohexylamine.

The invention also relates to the use of secondary amines of the three aliphatic, aromatic and cyclic classes bearing functional substituents on the alkyl, aryl or cycloalkyl groups attached to nitrogen. Of the possible substituents, the carboxylic acid and halogen functions, another amine function (primary, secondary or tertiary), ether, ester, oxime, nitro, nitrile, sulphonate, ketone and aldehyde are, for example, suitable.

An examination of the effect of the amine:hydrogen peroxide molar ratio has shown that the higher this ratio, the greater the hydroxylamine yield with respect to the quantity of $H_2O_2$ employed, this yield being defined by the relation:

$$\frac{\text{Number of moles of hydroxylamine formed}}{\text{Number of moles of } H_2O_2 \text{ employed}} \times 100$$

Amine:hydrogen peroxide molar ratios between 1.5 and 10 are highly suitable. Molar ratios between 2.5 and 4 are preferred because they mean that only the amine has to be recycled, the rate of conversion of $H_2O_2$:

$$\frac{\text{Number of moles of } H_2O_2 \text{ consumed}}{\text{Number of moles of } H_2O_2 \text{ employed}} \times 100$$

being approximately 100%. In practice, it is advisable to keep the amine:hydrogen peroxide molar ratio in the region of 2.8 so as not to have to recycle an excessively large quantity of amine.

Hydrogen peroxide can be employed in the form of a commercial aqueous solution or in the form of a solution in an organic solvent. Aqueous solutions are generally preferred because of their lower cost and their greater availability. Aqueous solutions containing at least 10% by weight and not more than 95% by weight of hydrogen peroxide are highly suitable. Solutions containing between 20 and 85% by weight hydrogen peroxide are used in preference.

In the process according to the invention, oxidation can be carried out to advantage in a liquid medium in an inert solvent.

It is generally advantageous for the liquid medium to be obtained by dissolving the secondary amine, hydrogen peroxide and the catalyst in an inert solvent. It is not necessary for the catalyst to be completely dissolved, its presence in the dispersed state in the liquid medium being sufficient.

The function of the inert solvent of the process according to the invention is to provide a homogeneous liquid medium capable, under the reaction conditions, of solubilising the secondary amine, hydrogen peoxide and the hydroxylamine formed. It must be inert towards the amine, hydrogen peroxide and the oxidation products. It can be water or an organic solvent resistant to oxidation by hydrogen peroxide under the reaction conditions. The most advantageous organic solvents are those whose dielectric constant at 25° C. and at atmospheric pressure is greater than 15.

DESCRIPTION OF THE PREFERRED EMBODIMENTS

In a preferred embodiment of the process according to the invention, the solvent chosen consists of water. A part of this may be introduced with the reagents, particularly with hydrogen peroxide; after all, it is also formed during the oxidation of the amine.

In a variant of this embodiment, one or more organic solvents are mixed in order to facilitate dissolution of the amine, hydrogen peroxide and the hydroxylamine. Solvents which are highly suitable include, for example, the lower aliphatic alcohols, possibly substituted, such as methanol, ethanol, isopropanol, n-butanol and trifluoroethanol, glycols such as ethylene glycol, 1,3-butanediol, 1,4-butanediol and 2,3-butanediol, glycerol, ethers such as diethylether and 1,4-dioxane and amides such as formamide, acetamide and N,N-dimethylformamide.

It has been observed that, in addition to its function of polar solvent, water has a favourable effect on the hydroxylamine yield with respect to hydrogen peroxide and that it was consequently advantageous to maintain in the reaction medium a not inconsiderable quantity of water and, advantageously, more than 10% by weight of the reaction mixture.

In a particular method of execution of this variant of the process according to the invention, catalytic oxidation of the secondary amine is carried out in a 2-phase system of water/organic phase using the method of phase transfer catalysis. This method is particularly advantageous if the catalyst or the amine is virtually insoluble in water.

The temperature and pressure at which the oxidation reaction according to the invention is carried out can vary widely. Although these limits are not critical, a range of optimum conditions is, however, observed, particularly in the case of the temperature, said conditions depending on the nature of the secondary amine, its concentration and that of hydrogen peroxide, the composition of the solvent and the other operating conditions in general. The optimum temperatures and pressures must be determined carefully in each particular case envisaged. This determination can be carried out in a laboratory with the aid of routine synthesis tests.

The duration of the oxidation reaction depends on the nature of the amine to be oxidised and the catalyst and the solvent employed. It can vary between 10 and 90 minutes. Preferably, the reaction time is more than 30 minutes and does not exceed 75 minutes.

The process according to the invention can be carried out continuously or batchwise, in a single reactor or in a series of reactors arranged in parallel or in series. In order to carry out the process according to the invention, any equipment suitable for liquid reaction mixtures can be used.

The catalyst and the reagents can be introduced in various ways known in themselves. It is thus possible to carry out a single introduction, a continuous introduction or a stepwise introduction of the catalyst, the secondary amine and/or hydrogen peroxide.

A particularly preferred embodiment of the invention consists in mixing the solvent, catalyst and secondary amine beforehand, then introducing hydrogen peroxide into the mixture with agitation within a relatively short time not exceeding 20 minutes and preferably of the order of 5 to 10 minutes.

After reaction, the reaction mixture can undergo various methods of separation such as distillation and separation in order to collect the hydroxylamine and the unconverted reagents which can be recycled advantageously to the process.

If the process according to the invention is carried out continuously, the equipment described and illustrated in French Pat. No. FR-B-8112797 filed on 26 June 1981 (INTEROX-Société Anonyme) can be used to advantage.

The invention also relates to the di-substituted N,N-hydroxylamines obtained by the process described above, as industrial products.

The di-substituted N,N,-hydroxylamines produced by the process according to the invention can be used as intermediates in various organic syntheses. They are also used as olefin polymerisation inhibitors in the rubber industry by virtue of their property of capturing free radicals, as oxygen inhibitors in boilers, as pharmaceuticals and as stabilisers of styrene.

Details of the invention will be derived from the following examples which describe processes for the preparation of di-substituted N,N-hydroxylamines in conformity with the invention and comparative tests with known processes.

EXAMPLE 1R (known reference process)

A quantity of 40 ml (0.387 mole) of diethylamine and 38 ml water was introduced at ambient temperature into a double-jacketed 500 ml glass reactor allowing heating by oil circulation and fitted with a cooling coil, via a feed aperture situated in the upper part of the reactor. After the reactor had been closed again, the temperature of the reaction medium was raised to 60° C. and 12 ml of an aqueous solution containing 40% by weight hydrogen peroxide (0.20 mole) were then introduced continuously over a period of 6 minutes. The mixture was then left to react for 45 minutes and the heating of the double jacket was then stopped and the medium cooled with fresh water which was circulated in the cooling coil.

When the reaction liquid had been brought back to ambient temperature, 10 ml of dioxane were introduced as an internal standard for the chromatographic analysis, and the mixture was then homogenised.

The reaction liquid was then analysed by the method of vapour-phase chromatography (capillary column made of vitreous silica, carrier gas helium). 0.168 mole of N,N-diethylhydroxylamine was determined in the medium, which corresponds to an N,N-diethylhydroxylamine yield of 56.6% with respect to the $H_2O_2$ used.

EXAMPLE 2R (known reference process)

The same operating procedure as in example 1R was used except that 0.329 g $Na_2WO_4$ was added as a catalyst to the mixture of reagents.

A yield of 0.012 mole of N,N-diethylhydroxylamine was determined in the reaction products, namely a yield of 6.0% with respect to the $H_2O_2$ used.

EXAMPLE 3

(in accordance with the invention)

The same operating procedure as in example 2R was followed, except for the catalyst which, in this case, consisted of 0.021 g of $CdCl_2 \cdot 2H_2O$ (0.1 mmole of Cd).

0.134 mole of N,N-diethylhydroxylamine was determined in the reation mixture, namely a yield of 67.0% with respect to the $H_2O_2$ used.

This example when compared with examples 1R and 2R illustrates the effectiveness of the catalyst according to the invention.

EXAMPLES 4 to 15

(in accordance with the invention)

Examples 4 to 15 were carried out according to the invention using catalysts based on zinc and their purpose was to examine the effect of the quantity of catalyst.

The operating procedure followed was similar to the one in example 2R for all these tests.

The results of the chromatographic analyses made it possible to calculate the yields of hydroxylamine produced with respect to the quantity of $H_2O_2$ used (Y $H_2O_2$). These yields have been entered in table 1 below.

TABLE I

| Example No. | Nature of catalyst | Catalyst used mmole Zn | $Y_{H_2O_2}$ % |
| --- | --- | --- | --- |
| 4 | $ZnCl_2$ | 2.05 | 70 |
| 5 | | 1.26 | 73 |
| 6 | | 0.68 | 70 |
| 7 | | 0.34 | 69 |
| 8 | | 0.15 | 66 |
| 9 | | 0.03 | 67 |
| 10 | $2ZnCO_3 \cdot 3Zn(OH)_2$ | 1.37 | 75 |
| 11 | | 0.46 | 74 |
| 12 | | 0.05 | 69 |
| 13 | $Zn(CH_3-COO)_2 \cdot 2H_2O$ | 1.37 | 77 |
| 14 | | 0.68 | 70 |
| 15 | | 0.34 | 68 |

The yields obtained show the remarkable effectiveness of the catalyst even when its concentration in the medium is very low.

Moreover, they suggest a broadly similar performance for inorganic or organic derivatives of zinc.

EXAMPLES 16 to 20

(in accordance with the invention)

The purpose of these examples was to study the effect of the amine: $H_2O_2$ molar ratio on the Y $_{H_2O_2}$ yield defined above. These examples were carried out in the same equipment and following the same procedure as in test 1R. The particular conditions of tests 16 to 20 were as follows:

| | |
| --- | --- |
| Solvent: $H_2O$ | 50 ml |
| Amine: $(CH_3-CH_2)_2-NH$ | 0.852 mole |
| $H_2O_2$: 84% by weight | quantity variable according to the test |
| Catalyst: $2ZnCO_3 \cdot 3Zn(OH)_2$ | 2.2 mmoles of Zn |
| $H_2O_2$ introduction time: | 15 minutes |
| Reaction temperature | 60° C. |
| Reaction time: | 60 minutes. |

The yields determined by vapour phase chromatography are shown in table II.

TABLE II

| Example Number | Amine:$H_2O_2$ molar ratio | $Y_{H_2O_2}$% |
| --- | --- | --- |
| 16 | 1.75 | 63 |
| 17 | 2.20 | 71 |
| 18 | 2.90 | 75 |
| 19 | 4.40 | 80 |
| 20 | 8.80 | 86 |

EXAMPLES 21 to 23

(in accordance with the invention)

In examples 21 to 23, all in accordance with the invention, the aim was to study the effect of the reaction temperature on the N,N-diethylhydroxylamine yield $Y_{H_2O_2}$.

The particular conditions of test 21 to 23 were as follows:

| | |
| --- | --- |
| Solvent : $H_2O$ | 30 ml |
| Amine: $(CH_3-CH_2)_2-NH$ | 0.852 mole |
| $H_2O_2$ : 84% by weight | 0.300 mole |
| Catalyst: $2ZnCO_3 \cdot 3Zn(OH)_2$ | 2.25 mmoles of Zn |
| $H_2O_2$ introduction time | 45 minutes |
| Reaction time | 60 minutes |

The results obtained were entered in table III.

The results obtained were entered in table III.

TABLE III

| Example | Reaction temperature °C. | $Y_{H_2O_2}$% |
| --- | --- | --- |
| 21 | 50 | 35 |
| 22 | 60 | 71 |
| 23 | 70 | 65 |

EXAMPLES 24 to 28

(in accordance with the invention)

These examples were carried out in order to study the effect of the reaction time on the N,N-diethylhydroxylamine yield $Y_{H_2O_2}$. The particular conditions of these examples were as follows:

| | |
| --- | --- |
| Solvent: $H_2O$ | 50 ml |

| | |
|---|---|
| Amine: (CH$_3$—CH$_2$)$_2$—NH | 0.852 mole |
| H$_2$O$_2$: 84% by weight | 0.300 mole |
| Catalyst: 2ZnCO$_3$.3Zn(OH)$_2$ | 2.25 mmoles of Zn |
| H$_2$O$_2$ introduction time | 6 minutes |
| Reaction temperature | 60° C. |

The results obtained are shown in table IV.

TABLE IV

| Example Number | Reaction Time Min. | Y$_{H_2O_2}$ % |
|---|---|---|
| 24 | 15 | 23.5 |
| 25 | 30 | 73.5 |
| 26 | 45 | 75.0 |
| 27 | 60 | 75.05 |
| 28 | 90 | 75.1 |

EXAMPLES 29R (known reference process)

This example illustrates the synthesis of di-n-propyl-hydroxylamine by the known process of oxidation with hydrogen peroxide in the absence of catalyst.

The operating procedure was similar to the one used in example 1R. The particular conditions of example 29R were, however:

| | |
|---|---|
| Solvent: CH$_3$OH | 60 ml |
| Amine: (CH$_3$—CH$_2$—CH$_2$)$_2$—NH | 0.718 mole |
| H$_2$O$_2$: 84% by weight | 0.264 mole |
| H$_2$O$_2$ introduction time | 10 minutes |
| Reaction temperature | 75° C. |
| Internal standard introduced for VPC analysis: cyclohexanol, | 10 g |

The analysis of the reaction medium by the method of vapour phase chromatography indicated an N,N-di-n-propylhydroxylamine yield Y $_{H_2O_2}$ of 8.7% with respect to the hydrogen peroxide used.

EXAMPLES 30 to 33

(in accordance with the invention)

These examples were carried out with a view to studying the effect of the reaction time on the N,N-di-n-propylhydroxylamine yield Y$_{H_2O_2}$.

The operating procedure used was that of example 2R. The particular conditions of examples 30 to 33 were:

| | |
|---|---|
| Solvent: CH$_3$OH | 60 ml |
| Amine: (CH$_3$—CH$_2$CH$_2$)$_2$—NH | 0.718 mole |
| H$_2$O$_2$: 84% by weight | 0.264 mole |
| Catalyst: 2ZnCO$_3$.3Zn(OH)$_2$ | 0.46 mmoles of Zn |
| H$_2$O$_2$ introduction time | 10 minutes |
| Reaction temperature | 75° C. |

The results were entered in table V.

TABLE V

| Example Number | Reaction time min. | Y$_{H_2O_2}$% |
|---|---|---|
| 34 | 30 | 53.0 |
| 35 | 45 | 59.0 |
| 36 | 60 | 62.0 |
| 37 | 75 | 63.5 |

We claim:

1. Process for the preparation of disubstituted N,N-hydroxylamines comprising the steps of oxidizing a secondary amine with hydrogen peroxide in the presence of a catalyst, said catalyst essentially consisting of at least one anion selected from the group consisting of hydroxide, halide, carbonate, and carboxylate having from one to seven carbon atoms, and at least one cation selected from the group consisting of zinc and cadmium; and recovering said disubstituted N,N-hydroxylamine.

2. Process according to claim 1, wherein the oxidizing step is carried out in an inert solvent medium chosen from the group consisting of water and organic solvents whose dielectric constant is more than 15 at atmospheric pressure and at a temperature of 25° C.

3. Process according to claim 1, wherein the secondary amine is chosen from the group consisting of aliphatic amines and aromatic amines.

4. Process according to claim 1, wherein the hydrogen peroxide used is an aqueous solution containing more than 10% by weight and less than 95% by weight hydrogen peroxide.

5. Process according to claim 1, wherein the catalyst is used in a quantity of between 0.02 and 10 mmoles per mole of amine used.

6. Process according to claim 1, wherein the amine:hydrogen peroxide molar ratio is kept between 1.5 and 10.

7. Process according to claim 1, wherein the reaction is carried out at a temperature of between 50° and 80° C. at atmospheric pressure for a period of between 30 and 75 minutes.

* * * * *